United States Patent [19]

Walker et al.

[11] 4,316,017

[45] Feb. 16, 1982

[54] CEPHALOSPORIN INTERMEDIATES

[75] Inventors: Derek Walker, Jamesville; Herbert H. Silvestri, DeWitt; Chester Sapino, East Syracuse; David A. Johnson, Fayetteville, all of N.Y.

[73] Assignee: Bristol-Myers Company, New York, N.Y.

[21] Appl. No.: 158,546

[22] Filed: Jun. 11, 1980

Related U.S. Application Data

[60] Continuation-in-part of Ser. No. 110,277, Jan. 7, 1980, abandoned, which is a division of Ser. No. 21,511, Mar. 19, 1979, Pat. No. 4,223,135.

[51] Int. Cl.$^3$ .......................................... C07D 501/36
[52] U.S. Cl. .................................. 544/026; 424/246; 544/27
[58] Field of Search ............................ 544/16, 27, 28

[56] References Cited

U.S. PATENT DOCUMENTS

| | | | |
|---|---|---|---|
| 3,516,997 | 6/1970 | Takano et al. | 260/243 C |
| 3,641,021 | 2/1972 | Ryan | 260/243 C |
| 3,671,449 | 6/1972 | Jackson | 260/243 C |
| 3,694,437 | 9/1972 | Jackson | 260/243 C |
| 3,741,959 | 6/1973 | Looker et al. | 260/243 C |
| 3,819,623 | 6/1974 | Takano et al. | 260/243 C |
| 3,828,037 | 8/1974 | Marinis et al. | 260/243 C |
| 3,867,380 | 2/1975 | Dunn et al. | 260/243 C |
| 3,928,336 | 12/1975 | Essery et al. | 260/243 C |
| 3,965,098 | 6/1976 | Robinson | 260/243 C |
| 4,051,131 | 9/1977 | Robinson | 544/28 |
| 4,100,346 | 7/1978 | Gottstein et al. | 544/27 |

FOREIGN PATENT DOCUMENTS 1073530 6/1977 United Kingdom .

OTHER PUBLICATIONS

Breederveld, H. Recveil, vol. 79 1126 (1960).
Cragg, R. H., J. Chem. Soc. A pp. 82–85 (1966).
Kricheldorf, H. R. CA vol. 73 45820r (1970).
Kricheldorf, H. R. CA vol. 74 54156b (1971).
Mironov et al., 2H OB SHCH KHIM 45 pp. 1971–1973 (1975).
Sheludyakov et al., 2H OB SHCH KHIM 45471 (1975).
Mironov et al., 2H OBSHCH KHIM 46 pp. 2297–2298 (1976).
Oertel et al., CA 60 6868b (1964).

*Primary Examiner*—Nicholas S. Rizzo
*Attorney, Agent, or Firm*—Herbert W. Taylor, Jr.

[57] ABSTRACT

In the preferred embodiment of the present invention trimethylsilyl 7-trimethylsilyloxycarbonylaminodecephalosporanate was prepared by bubbling dry carbon dioxide into an anhydrous solution of trimethylsilyl 6-trimethylsilylaminodecephalosporanate and found to be a useful intermediate in the production of cefadroxil and cephalexin by its acylation in anhydrous media with the appropriate 2-phenylglycyl chloride hydrochloride. Other cephalosporins are produced by acylation of 7-trimethylsilyloxycarbonylaminoceph-3-em-4-carboxylic acids or esters having a variety of substituents at the 3-position.

3 Claims, No Drawings

CEPHALOSPORIN INTERMEDIATES

CROSS-REFERENCE TO RELATED APPLICATIONS

This application is a continuation-in-part of our prior, co-pending application Ser. No. 110,277 filed Jan. 7, 1980 and now abandoned, which was in turn a divisional of our prior, co-pending application Ser. No. 21,511 filed Mar. 19, 1979 and issued Sept. 16, 1980 as U.S. Pat. No. 4,223,135.

BACKGROUND OF THE INVENTION

1. Field of the Invention

The chemical processes of the present invention produce antibacterial agents of the class commonly called cephalosporins or intermediates for said production.

2. Description of the Prior Art

The patent literature alone contains a large number of disclosures of the production of cephalosporins by the reaction with a silylated nucleus [such as 7-aminocephalosporanic acid (7-ACA) or 7-aminodesacetoxycephalosporanic acid] of a sidechain acid in the form of its acid chloride. When that acid contains a free amino group such group is preferably blocked, as by protonation, and so use is made, for example, of 2-phenylglycylchloride hydrochloride to make cephalexin. The 4-carboxyl group of the nucleus may be blocked by silylation or by esterification. Some examples of such patents are U.S. Pat. Nos. 3,671,449, 3,694,437, 3,741,959, 3,957,773, 3,965,098, 4,051,131 and U.K. Pat. No. 1,073,530. In many instances the 3-acetoxy group of 7-ACA has been displaced before acylation by a heterocyclic thiol, e.g. ceforanide (U.S. Pat. No. 4,100,346 and see the description of prior art therein), cefatrizine (U.S. Pat. No. 3,867,380), cefaparole (U.S. Pat. No. 3,641,021), cefazolin (U.S. Pat. Nos. 3,516,997 and 3,819,623), cefazaflur (U.S. Pat. No. 3,828,037) and the like or by other types of thiols as reviewed in U.S. Pat. No. 3,928,336.

A search of Chemical Abstracts Formula Indexes Vols. 58-87 showed that I had not been indexed.

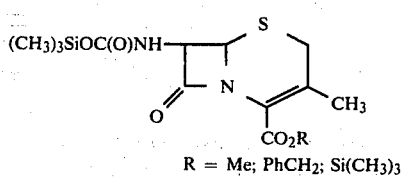

R = Me; PhCH₂; Si(CH₃)₃

Siloxycarbonylamino derivatives are indexed under silanol, carbamic acid and under N-carboxy derivatives of compounds as the trimethylsilyl ester.

However, the following papers appear of some interest:

1. Breederveld, H.: The interaction of dialkylaminosilanes with carbon disulphide. A novel reaction in organosilicon chemistry. Recueil, 79, 1126 (1960).

2. Cragg, R. H.; Lappert, M. F.: Aminoderivatives of metals and metalloids. Part IV. Aminosilylation and aminophosphination of some unsaturated substrates. J. Chem. Soc. (A), 82-85 (1966).

3. Kricheldorf, H. R.: Herstellung von N-Silyloxycarbonylaminosaure-derivaten. Synthesis, 259-60 (1970) (Ger.): C.A. 73, 45820r (1970).

4. Kricheldorf, H. R.: The preparation of amino acid N-carboxyanhydrides (NCAs) from N-siloxycarbonyl amino acid trimethylsilyl esters. Chem. Ber., 104, 87-91 (1971) (Ger.); C.A. 74, 54156b (1971).

5. Mironov, V. F.; Kozyukov, V. P.; Kirilin, A. D., et al.: Synthesis and reactions of silyl carbamates. New method for the preparation of organic isocyanates without the use of phosgene. Zh Obshch Khim, 45, 1971-1973 (1975).

6. Sheludyakov, V. D.; Kirilin, A. D.; Mironov, V. F.: New method for the preparation of (carbamoyloxy)-silanes. Zh Obshch Khim, 45, 471 (1975).

7. Mironov, V. F.; Sheludyakov, V. D.; Kirilin, A. D.: Siloxycarbonylation of amines. Zh Obshch Khim, 46, 2297-98 (1976).

8. Farbenfabriken Bayer A-G (Oertel, G., et al.): Organosilicon compounds. Chem. Abs., 60, 6868b. (Ger. Offen. No. 1,157,226).

SUMMARY OF THE INVENTION

There is provided by the present invention a compound having the formula

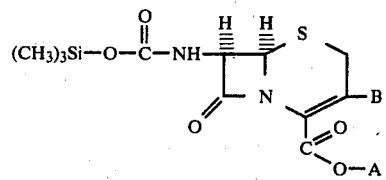

wherein B is chloro, methoxy or —CH₂E;

A is (CH₃)₃Si— or an easily cleavable ester protecting group which is preferably selected from the group consisting of benzhydryl, benzyl, p-nitrobenzyl, p-methoxybenzyl, trichloroethyl, phenacyl, acetonyl, methoxymethyl, 5-indanyl, 3-phthalidyl, pivaloyloxymethyl and acetoxymethyl; 1-[(ethoxycarbonyl)oxy]ethyl; and E is hydrogen,

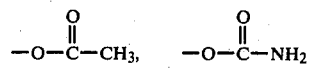

or —S—Z wherein Z represents a 5- or 6-membered, and preferably a 5-membered, aromatic heterocyclic ring containing two, three or four atoms of N and zero or one atom selected from the group consisting of O and S, said heterocyclic ring being optionally substituted by one or two and preferably one substituent selected from the group consisting of halo, C₁-C₄ alkyl and preferably methyl, C₁-C₄ alkoxy, cyano, nitro, C₃-C₄ cycloalkyl, C₂-C₄ alkenyl, trifluoromethyl, C₁-C₄ alkylthio, di(C₁-C₄ alkyl)amino, phenyl, benzyl, alkoxyalkyl of up to 4 carbons, —COOSi(CH₃)₃ and —(CH₂)ₙCOOSi(CH₃)₃ in which n is 1, 2 or 3 and preferably n is 1, said sulfur atom in —S—Z being connected to a carbon atom of said heterocyclic ring Z and said aromatic heterocyclic ring is preferably a triazole, tetrazole, oxadiazole or thiadiazole.

Preferred individual embodiments of the present invention are those in which A is (CH₃)₃Si and E is hydrogen,

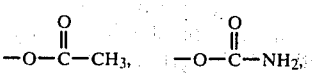

-continued

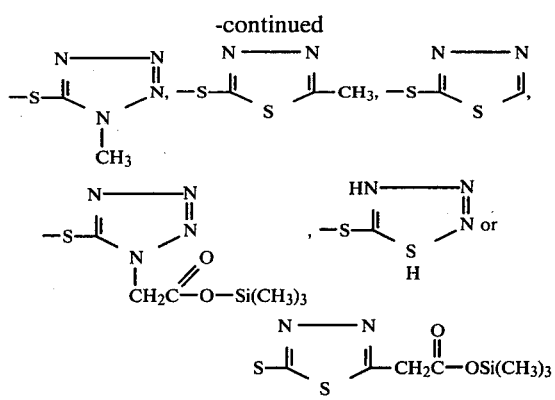

There is also provided by the present invention the process for the production of a compound of the formula

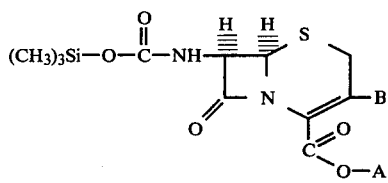

wherein B is chloro, methoxy or —CH₂E;

A is (CH₃)₃Si— or an easily cleavable ester protecting group; and

E is hydrogen,

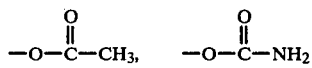

or —S—Z wherein Z represents a 5- or 6-membered aromatic heterocyclic ring containing two, three or four atoms of N and zero or one atom selected from the group consisting of O and S, said heterocyclic ring being optionally substituted by one or two substituents selected from the group consisting of halo, $C_1$-$C_4$ alkyl, $C_1$-$C_4$ alkoxy, cyano, nitro, $C_3$-$C_4$ cycloalkyl, $C_2$-$C_4$ alkenyl, trifluoromethyl, $C_1$-$C_4$ alkylthio, di($C_1$-$C_4$ alkyl)amino, phenyl, benzyl, alkoxyalkyl of up to 4 carbons, —COOSi(CH₃)₃ and —(CH₂)ₙCOOSi(CH₃)₃ in which n is 1, 2 or 3, said sulfur —(CH₂)ₙCOOSi(CH₃)₃ in which n is 1, 2 or 3, said sulfur atom in —S—Z being connected to a carbon atom of said heterocyclic ring Z which comprises adding dry carbon dioxide to a solution of a compound having the formula

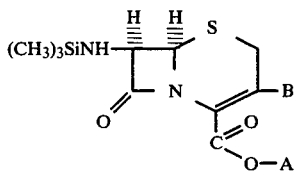

wherein B is chloro, methoxy or —CH₂E;

A is (CH₃)₃Si— or an easily cleavable ester protecting group which is preferably selected from the group consisting of benzhydryl, benzyl, p-nitrobenzyl, p-methoxy-5-indanyl, 3-phthalidyl, pivaloyloxymethyl and acetoxymethyl; 1-[(ethoxycarbonyl)oxy]ethyl; and E is hydrogen,

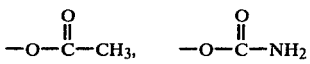

or —S—Z wherein Z represents a 5- or 6-membered, and preferably a 5-membered, aromatic heterocyclic ring containing two, three or four atoms of N and zero or one atom selected from the group consisting of O and S, said heterocyclic ring being optionally substituted by one or two and preferably one substituent selected from the group consisting of halo, $C_1$-$C_4$ alkyl and preferably methyl, $C_1$-$C_4$ alkoxy, cyano, nitro, $C_3$-$C_4$ cycloalkyl, $C_2$-$C_4$ alkenyl, trifluoromethyl, $C_1$-$C_4$ alkylthio, di($C_1$-$C_4$ alkyl)amino, phenyl, benzyl, alkoxyalkyl of up to 4 carbons, —COOSi(CH₃)₃ and —(CH₂)ₙCOOSi(CH₃)₃ in which n is 1, 2 or 3 and preferably n is 1, said sulfur atom in —S—Z being connected to a carbon atom of said heterocyclic ring Z and said aromatic heterocyclic ring is preferably a triazole, tetrazole, oxadiazole or thiadiazole in an anhydrous inert organic solvent and preferably in methylene chloride at a temperature in the range of 0° C. to 100° C. and preferably in the range of 0° C. to 20° C. until completion of the carboxylation reaction.

Preferred individual embodiments of that process are those in which A is (CH₃)₃Si, B is chloro, methoxy or —CH₂E and E is hydrogen,

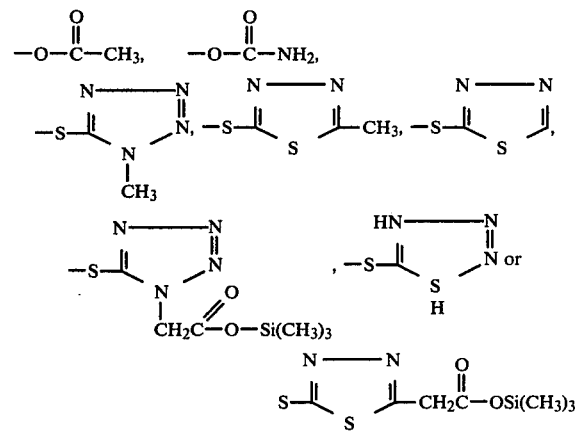

There is further provided by the present invention for use in the process for the production of a conventional cephalosporin having the formula

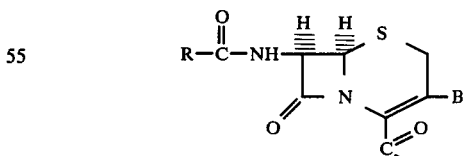

wherein

is the residue after removal of the hydroxyl group of an organic carboxylic acid containing from two to twenty carbon atoms, and B is chloro, methoxy or —CH₂E wherein E is hydrogen,

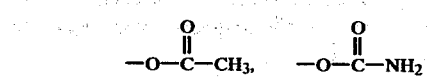

or —S—Z wherein Z represents a 5- or 6-membered, and preferably a 5-membered, aromatic heterocyclic ring containing two, three or four atoms of N and zero or one atom selected from the group consisting of O and S, said heterocyclic ring being optionally substituted by one or two and preferably one substituent selected from the group consisting of halo, $C_1$–$C_4$ alkyl and preferably methyl, $C_1$–$C_4$ alkoxy, cyano, nitro, $C_3$–$C_4$ cycloalkyl, $C_2$–$C_4$ alkoxy, trifluoromethyl, $C_1$–$C_4$ alkylthio, di(C₁–$C_4$ alkyl)amino, phenyl, benzyl, alkoxyalkyl of up to 4 carbons, —COOSi(CH₃)₃ and —(CH₂)ₙCOOSi(CH₃)₃ in which n is 1, 2 or 3 and preferably n is 1, said sulfur atom in —S—Z being connected to a carbon atom of said heterocyclic ring Z and said aromatic heterocyclic ring is preferably a triazole, tetrazole, oxadiazole or thiadiazole

*which comprises* the consecutive steps of *acylating* with the acid chloride of said organic carboxylic acid a silylated nucleus having the formula

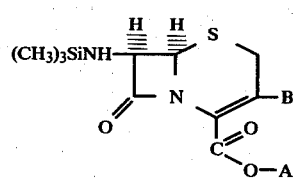

wherein A is (CH₃)₃Si— or an easily cleavable ester protecting group preferably selected from the group consisting of benzhydryl, benzyl, p-nitrobenzyl, p-methoxybenzyl, trichloroethyl, phenacyl, acetonyl, methoxymethyl, 5-indanyl, 1-[(ethoxycarbonyl)oxy]ethyl, 3-phthalidyl, pivaloyloxymethyl and acetoxymethyl, and B has the same meaning as above, *and then converting* group A to hydrogen and if desired removing any blocking group on A and B,

*the improvement* which comprises, prior to acylation, converting said silylated nucleus to a compound of the formula

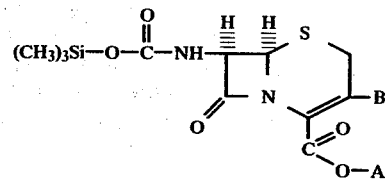

wherein A and B have the same meaning as above, by adding dry carbon dioxide to a solution of said silylated nucleus in an anhydrous inert organic solvent and preferably in methylene chloride at a temperature in the range of 0° to 100° C. and preferably in the range of 0° to 20° C. until completion of the carboxylation reaction.

Preferred embodiments of that process are those in which A is (CH₃)₃Si, B is chloro, methoxy or —CH₂E wherein E is hydrogen

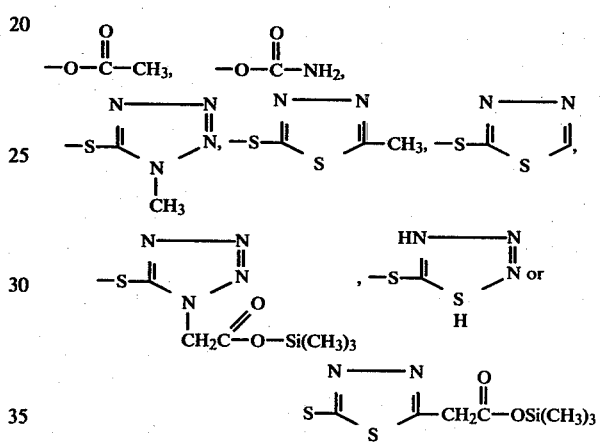

A conventional cephalosporin as defined herein is one which has been described previously in the patent or scientific literature, including abstracts thereof.

ILLUSTRATIVE PREPARATIONS OF REAGENTS

The following specific procedures are generally applicable to the preparation of 7-amino-3-heterocyclic-thiomethyl-ceph-3-em-4-carboxylic acids.

(a) 7-Amino-3-(1-carboxymethyltetrazol-5-yl-thiomethyl)-3-cephem-4-carboxylic acid

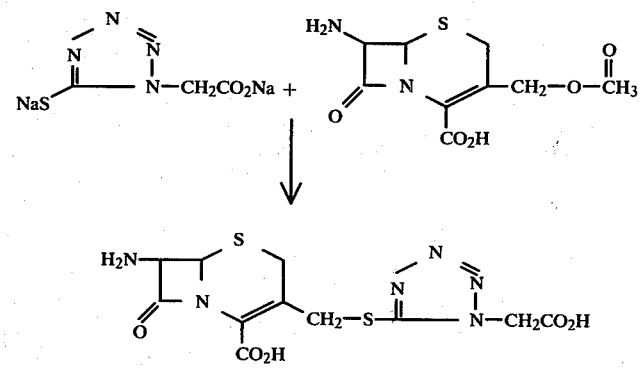

1. Into a 3 necked flask set up with an agitator, a temperature regulator, thermometer and a nitrogen inlet tube, place 18 grams (0.066 mole) of 7-aminocephalosporanic acid, (which has preferably been recrystallized by the toluenesulfonic acid procedure) and 300 ml. of 0.1 M pH 6.4 phosphate buffer (20.7 grams of sodium phosphate, monobasic 0.1H$_2$O+8.5 grams of sodium phosphate, dibasic, anhydrous, q.s. to 2 liters).

2. With agitation of the mixture described in step 1, add 1.5 grams of sodium bisulfite and 16 grams (0.078 moles) of 1-carboxymethyl-5-mercaptotetrazole disodium.

3. With agitation continuing, bubble nitrogen through the mixture for 10 minutes.

4. Maintaining agitation and nitrogen inflow, heat the slurry over a 20 minute period to 56° C. During this time interval, 6.5 grams of sodium bicarbonate is added in small increments.

5. With continued agitation and nitrogen inflow, maintain the temperature of the solution at 56° C. for 4 hours. The pH should remain at between 6.2–6.6.

6. Cool the reaction mixture in an ice bath to 5° C.

7. Add 50 ml. of a 1:1 phosphoric acid/water solution to the mixture or concentrated HCl to a pH of 2.0–3.0.

8. Collect the product by filtration. Wash the filter cake with 20 ml. of cold water followed by 200 ml. of cold methanol.

(b) 1. 2.72 g. of 7-aminocephalosporanic acid and 1.16 g. of 5-mercapto-1-methyl-1H-tetrazole are suspended in 14 ml. of anhydrous acetonitrile. Then 4.25 g. of boron trifluoride-diethyl ether complex salt is added and dissolved therein. The solution is heated at 50° C. for 2 hours to allow reaction to proceed. The reaction solution is cooled, 14 ml. of water is added and the pH is adjusted to 4.0 with ammonia water under iced condition. The deposited crystals are filtered off, washed with 5 ml. of water and then with 5 ml. of acetone, and thereafter dried to give 3.00 g. (91.5% yield) of 7-amino-3-[5-(1-methyl-1,2,3,4-tetrazolyl)-thiomethyl]-Δ$^3$-cephem-4-carboxylic acid, m.p. 224°–226° C. dec.

2. The following are the results of having substituted other boron trifluoride complex salts for the boron-trifluoride-diethyl ether complex salt used in the above 1:

| No. | Boron trifluoride complex salts (BF$_3$ contents, %) | Amount | Reaction Conditions | Yield |
|---|---|---|---|---|
| 1 | Acetic acid complex salt (about 40%) | 6.8 g. | 50° C., 2 hrs. | 82.5% |
| 2 | Phenol complex salt (about 25%) | 10.9 g. | 50° C., 2 hrs. | 77.5% |
| 3 | di-n-butyl ether complex salt (about 34%) | 6.0 g. | 50° C., 2 hrs. | 88.7% |
| 4 | Acetic acid complex salt | 2.4 g. | 0–5° C., 8 hrs. | 90.5% |

3. In the above 1, substitution of propionitrile for acetonitrile resulted in 87.8% yield.

4. In the above 1, substitution of sulforan for acetonitrile resulted in 90.5%, provided that the reaction conditions were 20° C., 10 hours.

5. In the above 1, if 1.25 ml. of 12 N hydrochloric acid is added to the reaction solution, stirring is made for 2 hours under iced condition and the deposited crystals are filtered off, washed with two 5 ml. portions of acetone and dried, there is obtained 3.20 g. (88.0% yield) of hydrochloric acid salt of 7-amino-3-[5-(1-methyl-1,2,3,4-tetrazolyl)-thiomethyl]-Δ$^3$-cephem-4-carboxylic acid, m.p. 184°–186° C. dec.

(c) In the manner of procedure b above, 5-mercapto-1-carboxymethyl-1,2,3,4-tetrazole is converted to 7-amino-3-[5-(1-carboxymethyl-1,2,3,4-tetrazolyl)thiomethyl]-ceph-3-em-4-carboxylic acid melting at 183° C. with decomposition.

Following the same procedures but replacing the thiol used therein with equimolar amounts of the thiols indicated below produces the respective products of the given formulae as follows:

Product of the Formula $$H_2N-\text{[β-lactam]}-CH_2-S-Z$$
COOH

| Thiol Regent | Z = |
|---|---|
| methyl mercaptan | methyl |
| ethyl mercaptan | ethyl |
| butyl mercaptan | butyl |
| pentyl mercaptan | pentyl |
| 1-chloroethyl mercaptan | 1-chloroethyl |
| 2-bromomethyl mercaptan | 2-bromoethyl |
| 2-nitroethyl mercaptan | 2-nitroethyl |
| 5-nitropentyl mercaptan | 5-nitropentyl |
| 3-cyano-n-propyl mercaptan | 3-cyano-n-propyl |
| 4-(dimethylamino)-n-butyl mercaptan | 4-(dimethylamino)-n-butyl |
| 3-chloro-2-methylbutyl mercaptan | 3-chloro-2-methylbutyl |
| benzethiol | phenyl |
| p-chlorobenzenethiol | p-chlorophenyl |
| 2,4,5-trichlorobenzenethiol | 2,4,5-trichlorophenyl |
| p-bromobenzenethiol | p-bromophenyl |
| 2,5-dichlorobenzenethiol | 2,5-dichlorophenyl |
| p-fluorobenzenethiol | p-fluorophenyl |
| m-methoxybenzenethiol | m-methoxyphenyl |
| p-methoxybenzenethiol | p-methoxyphenyl |
| p-nitrobenzenethiol | p-nitrophenyl |
| 2,3,5,6-tetrachlorobenzenethiol | 2,3,5,6-tetrachlorophenyl |
| benzyl mercaptan | benzyl |
| p-chlorobenzyl mercaptan | p-chlorobenzyl |
| phenethyl mercaptan | phenethyl |
| p-nitrobenzyl mercaptan | p-nitrobenzyl |
| p-methoxybenzyl mercaptan | p-methoxybenzyl |
| 1-naphthalenethiol | 1-naphthyl |
| 2-naphthalenethiol | 2-naphthyl |
| 4-chloro-1-naphthalenethiol | 4-chloro-1-naphthyl |
| 4-nitro-1-naphthalenethiol | 4-nitro-1-naphthyl |
| 2-thienyl mercaptan | 2-thienyl |
| 3-thienyl mercaptan | 3-thienyl |
| 2-furyl mercaptan | 2-furyl |
| 3-furyl mercaptan | 3-furyl |
| 6-bromo-3-pyridazinethiol | 6-bromopyridazin-3-yl |
| 3-pyridazinethiol | pyridazin-3-yl |
| 3-methyl-1-phenyl-5-pyrazolethiol | 3-methyl-1-phenylpyrazol-5-yl |
| imidazole-2-thiol | imidazol-2-yl |
| 1-methyl-5-nitro-2-imidazolethiol | 1-methyl-5-nitroimidazol-2-yl |
| thiazole-2-thiol | thiazol-2-yl |
| 5-methylthiazole-2-thiol | 5-methylthiazol-2-yl |
| oxazole-2-thiol | oxazol-2-yl |
| 5-methyloxazole-2-thiol | 5-methyloxazol-2-yl |
| 2-pyridinethiol | 2-pyridyl |
| 4-pyridinethiol | 4-pyridyl |
| 5-nitro-2-pyridinethiol | 5-nitro-2-pyridyl |
| 3-methyl-1-phenyl-5-pyrazolethiol | 3-methyl-1-phenyl-pyrazol-5-yl |
| 2-pyrazinethiol | pyrazin-2-yl |
| 4-pyrimidinethiol | pyrimidin-4-yl |
| 4-methyl-2-pyrimidinethiol | 4-methylpyrimid-2-yl |
| 3-methylisothiazole-5-thiol | 3-methylisothiazol-5-yl |
| isothiazole-5-thiol | isothiazol-5-yl |
| 1,2,3,4-thiatriazole-5-thiol | 1,2,3,4-thiatriazol-5-yl |
| 5-mercapto-3-methylthio-1,2,4-thiadiazole | 3-methylthio-1,2,4-thiadiazol-5-yl |
| 5-mercapto-3-methyl-1,2,4-thiadiazole | 3-methyl-1,2,4-thiadiazol-5-yl |
| 2-mercapto-1,3,4-thiadiazole | 1,3,4-thiadiazole-2-yl |
| 5-mercapto-2-ethyl-1,3,4-thiadiazole | 2-ethyl-1,3,4-thiadiazol-5-yl |
| 5-mercapto-2-n-butyl-1,3,4-thiadiazole | 2-n-butyl-1,3,4-thiadiazol-5-yl |
| 5-mercapto-2-trifluoromethyl-1,3,4-thiadiazole | 2-trifluoromethyl-1,3,4-thiadiazol-5-yl |

| Thiol Regent | Product of the Formula<br/><br/>Z = |
|---|---|
| 2-mercapto-5-p-chlorophenyl-1,3,4-thiadiazole | 5-p-chlorophenyl-1,3,4-thiadiazole-2-yl |
| 3-mercapto-1,2,4-thiadiazole | 1,2,4-thiadiazole-3-yl |
| 5-mercapto-1-butyltetrazole | 1-butyltetrazol-5-yl |
| 5-mercapto-1-phenyltetrazole | 1-phenyltetrazol-5-yl |
| 1-benzyl-1H-tetrazole-5-thiol | 1-benzyl-1H-tetrazol-5-yl |
| 5-mercapto-1H-tetrazole | 1h-tetrazol-5-yl |
| 5-mercapto-1-p-chlorophenyl-1H-tetrazole | 1-p-chlorophenyl-1H-tetrazol-5-yl |
| 2-mercapto-1,3,4-oxadiazole | 1,3,4-oxadiazol-2-yl |
| 2-mercapto-5-phenyl-1,3,4-oxadiazole | 5-phenyl-1,3,4-oxadiazol-2-yl |
| 2-mercapto-5-benzyl-1,3,4-oxadiazole | 5-benzyl-1,3,4-oxadiazol-2-yl |
| 5-mercapto-3-phenyl-1,2,4-oxadiazole | 3-phenyl-1,2,4-oxadiazol-5-yl |
| 2-mercapto-5-ethyl-1,3,4-oxadiazole | 5-ethyl-1,3,4-oxadiazol-2-yl |
| 2-mercapto-5-trifluoromethyl-1,3,4-oxadiazole | 5-trifluoromethyl-1,3,4-oxadiazol-2-yl |
| 1-methyl-5-mercapto-1,2,3-triazole | 1-methyl-1,2,3-triazol-5-yl |
| 1-ethyl-5-mercapto-1,2,3-triazole | 1-ethyl-1,2,3-triazol-5-yl |
| 4-methyl-5-mercapto-1,2,3-triazole | 4-methyl-1,2,3-triazol-5-yl |
| 4-allyl-3-mercapto-1,2,4-triazole | 4-allyl-1,2,4-triazol-3-yl |
| 4-ethyl-3-mercapto-1,2,4-triazole | 4-ethyl-1,2,4-triazol-3-yl |
| 3-mercapto-5-methyl-1,2,4-triazole | 5-methyl-1,2,4-triazol-3-yl |
| 3-mercapto-1,2,4-triazole | 1,2,4-triazol-3-yl |
| 4,5-diethyl-3-mercapto-1,2,4-triazole | 4,5-diethyl-1,2,4-triazol-3-yl |
| 1-cyclopropyl-3-mercapto-1,2,4-triazole | 1-cyclopropyl-1,2,4-triazol-3-yl |
| 3-mercapto-5-methoxymethyl-1,2,4-triazole | 5-methoxymethyl-1,2,4-triazol-3-yl |

Preferred reagents obtained in this fashion are those in which Z has the formula

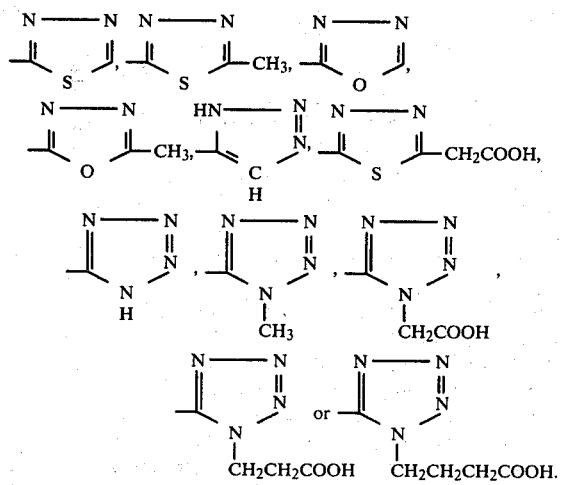

These products are then used to replace the 7-ADCA in Example 1 below and subsequent procedures.

The acid chlorides used in the examples below can be replaced by a variety of other acid chlorides to produce conventional cephalosporins. Such reaction is not limited to acylation of the product of Example 2 but includes acylation of the products obtained by the use in the procedures of Examples 1–8 of the thiols defined generally above and exemplified directly above.

Thus the acyl halide may be chosen to introduce any desired acyl group at the 7-amino position as is well known in the art, e.g. U.S. Pat. No. 3,741,959. It is thus possible to introduce specific acyl radicals including, but not limited to, those defined in the following general formulae:

(i) $R^u C_n H_{2n} CO-$ where $R^u$ is aryl (carboxylic or heterocyclic), cycloalkyl, substituted aryl, substituted cycloalkyl, or a non-aromatic or mesoionic heterocyclic group, and n is an integer from 1–4. Examples of this group include phenylacetyl, substituted phenylacetyl, e.g. fluorophenylacetyl, nitrophenylacetyl, aminophenylacetyl, acetoxyphenylacetyl, methoxyphenylacetyl, methphenylacetyl, or hydroxyphenylacetyl; N,N-bis(2-chloroethyl)aminophenylpropionyl; thien-3- and -3-acetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group, the aryl group being, e.g. phenyl or halophenyl, e.g. chloro- or bromophenyl. An acyl group of this type is 3-o-chlorophenyl-5-methyl isoxazol-4-yl-acetyl.

(ii) $C_n H_{2n+1} CO-$ wherein n is an integer from 1–7. The alkyl group may be straight or branched, and if desired, may be interrupted by an oxygen or sulphur atom or substituted by, e.g. a cyano group. Examples of such groups include cyanoacetyl, hexanoyl, heptanoyl, octanoyl and butylthioacetyl.

(iii) $C_n H_{2n-1} CO-$ wherein n is an integer from 2–7. The group may be straight or branched and, if desired, may be interrupted by an oxygen or a sulphur atom. An example of such a group is allylthioacetyl.

 (iv)

where $R^u$ has the meaning defined under (i) and in addition may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, 2-phenoxypropionyl, 2-phenoxybutyryl, benzyloxycarbonyl, 2-methyl-2-phenxypropionyl, p-cresoxyacetyl and p-methylthiophenoxyacetyl.

$$R^u S - \underset{R^w}{\overset{R^v}{C}} - CO- \quad (v)$$

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

(vi) $R^u Z(CH_2)_m CO-$ where $R^u$ has the meaning defined under (i) and, in addition, may be benzyl, Z is an oxygen or sulphur atom and m is an integer from 2–5. An example of such a group is S-benzylthiopropionyl.

(vii) $R^u CO-$ where $R^u$ has the meaning defined under (i). Examples of such groups include benzoyl, substituted benzoyl (e.g. aminobenzoyl), 4-isoxazolyland substituted 4-isoxazolyl carbonyl, cyclopentanecarbonyl, sydone carbonyl, naphthoyl and substituted naphthoyl (e.g. 2-ethoxynapthoyl) quinoxalinylcarbonyl and substituted quinoxalinylcarbonyl (e.g. 3-carboxy-2-quinoxalinylcarbonyl). Other possible substituents for benzoyl include alkyl, alkoxy, phenyl or phenyl substituted with carboxy, alkylamido, cycloalkylamido, allylamido, phenyl(lower)alkylamido, morpholinocarbonyl, pyrrolidinocarbonyl, piperidinocarbonyl, tetrahydropyridino, furfurylamido or N-alkyl-N-anilino, or derivatives thereof, and such substituents may be in the 2- or 2- and 6-positions. Examples of such substituted benzoyl groups are 2,6-dimethoxybenzoyl, 2-biphenylcarbonyl, 2-methylamidobenzoyl and 2-carboxybenzoyl. Where the group $R^u$ represents a substituted 4-isoxazolyl group, the substitutents may be as set out above under (i). Examples of such 4-isoxazol groups are 3-phenyl-5-methylisoxazol-4-yl carbonyl, 3-o-chlorophenyl-5-methyl isoxazol-4-yl carbonyl and 3-(2,6-dichlorophenyl)-5-methylisoxazol-4-yl carbonyl.

(viii)

where $R^u$ has the meaning defined under (i) and X is amino, substituted amino (e.g. acylamido or a group obtained by reacting the amino group and/or group(s) of the 7-sidechain with an aldehyde or ketone, e.g. acetone, methylethylketone or ethyl acetoacetate), hydroxy, carboxy, esterified carboxy, triazolyl, tetrazolyl, cyano, halogeno, acyloxy, (e.g. formyloxy or lower alkanoyloxy) or etherified hydroxy group. Examples of such acyl groups are α-aminophenylacetyl, α-carboxyphenylacetyl and 2,2-dimethyl-5-oxo-4-phenyl-1-imidazolidinyl.

(ix)

where $R^x$, $R^y$ and $R^z$ which may be the same or different may each represent lower alkyl, phenyl or substituted phenyl. An example of such an acyl group is triphenylcarbonyl.

(x)

where $R^u$ has the meaning defined under (i) and in addition may be hydrogen, lower alkyl or halogen substituted lower alkyl, and Y represents oxygen or sulphur. An example of such a group is $Cl(CH_2)_2NHCO$.

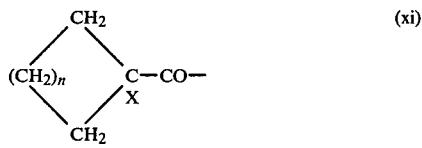
(xi)

where X has the meaning defined under (viii) above and n is an integer of from 1 to 4. An example of such an acyl group is 1-amino-cyclohexanecarbonyl.

(xii) Amino acyl, for example $R^wCH(NH_2).(CH_2)_nCO$ where n is an integer from 1-10, or $NH_2.C_nH_{2n}Ar(CH_2)_mCO$, where m is zero or an integer from 1-10, and n is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British patent specification No. 1,054,806. A group of this type is the p-aminophenylacetyl group. Other acyl groups of this type include those, e.g. δ-aminoadipoyl derived from naturally occurring amino acids and derivatives thereof, e.g. N-benzoyl-δ-aminoadipoyl.

(xiii) Substituted glyoxylyl groups of the formula $R^y.CO.CO$— where $R^y$ is an aliphatic, araliphatic or aromatic group, e.g. a thienyl group, a phenyl group, or a mono-, di- or tri-substituted phenyl group, the substituents being, for example, one or more halogen atoms (F, Cl, Br, or I), methoxy groups, methyl groups, or amino groups, or a fused benzene ring.

When the acyl group being introduced contains an amino group it may be necessary to protect this during the various reaction stages. The protecting group is conveniently one which can be removed by hydrolysis without affecting the rest of the molecule, especially the lactam and 7-amido linkages. The amine protecting group and the esterifying group at the 4—COOH position can be removed using the same reagent. An advantageous procedure is to remove both groups at the last stage in the sequence. Protected amine groups include urethane, arylmethyl (e.g. trityl)amino, arylmethyleneamino, sulphenylamino or enamine types. Enamine blocking groups are particularly useful in the case of o-aminomethylphenyl acetic acid. Such groups can in general be removed by one or more reagents selected from dilute mineral acids, e.g. dilute hydrochloric acid, concentrated organic acids, e.g. concentrated acetic acid, trifluoroacetic acid, and liquid hydrogen bromide at very low temperatures, e.g. −80° C. A convenient protecting group is the t-butoxycarbonyl group, which is readily removed by hydrolysis with dilute mineral acid, e.g. dilute hydrochloric acid, or preferably with a strong organic acid (e.g. formic acid or trifluoroacetic acid) e.g. at a temperature of 0°-40° C., preferably at room temperature (15°-25° C.). Another convenient protecting group is the 2,2,2-trichloroethoxycarbonyl group which may be split off by an agent such as zinc/acetic acid, zinc/formic acid, zinc/lower alcohols or zinc/pyridine.

The $NH_2$ group may also be protected as $NH_3^+$ by using the amino acid halide as an acid addition salt under conditions in which the amino group remains protonated.

The acid used to form the acid addition salt is preferably one having a $pK_a$ (in water at 25° C.) of $\not> x+1$, where x is the $pK_a$ value (in water at 25° C.) of the carboxy groups of the amino acid; the acid is preferably monohydric. In practice the acid HQ (see below) will generally have a $pK_a < 3$, preferably <1.

Particularly advantageous results have been found to accrue from the process according to the invention when the acyl halide is a salt of an amino acid halide. Amino acid halides have the formula

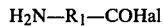

wherein $R_1$ is a divalent organic group and Hal is chloride or bromide. Salts of such amino acid halides have the formula

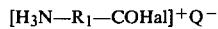

wherein R₁ and Hal have the above defined meanings and Q⁻ is the anion of the acid, HQ having a pK_a as defined above. The acid HQ is preferably a strong mineral acid such as, for example, a hydrohalic acid such as hydrochloric acid or hydrobromic acid. An important amino acid halide, by reason of the valuable cephem antibiotics which contain the group derived therefrom is D-N-(α-chlorocarbonyl-α-phenyl)methylammonium chloride, D-[PhCH(NH₃)COCl]⁺Cl⁻, which is referred to herein as D-α-phenylglycylchloride hydrochloride for convenience.

Cephalosporin compounds obtained by the process according to the invention and having the acylamido group R$^u$CH(NH₂)CONH— where R$^u$ has the above-defined meaning, may be reacted with a ketone R².R³CO where R² and R³ are lower alkyl groups (C₁-C₄), to yield compounds believed to contain the group:

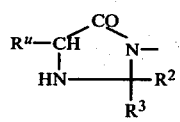

Compounds of this type include hetasporin and hetacephalexin.

Also included herein and incorporated in full by reference are the acyl groups set forth in U.S. Pat. No. 4,013,648 in columns 7-20 inclusive.

When the acylation process of the present invention is used to produce cephalosporins the final products are isolated and purified according to conventional methods well-known in the art.

Preferred acyl chlorides used in the present invention to acylate a compound having the formula

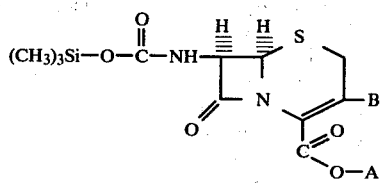

wherein B is chloro, methoxy or —CH₂E;
A is (CH₃)₃Si— or an easily cleavable ester protecting group; and
E is hydrogen,

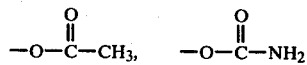

or —S—Z wherein Z represents a 5- or 6-membered aromatic heterocyclic ring containing two, three or four atoms of N and zero or one atom selected from the group consisting of O and S, said heterocyclic ring being optionally substituted by one or two substituents selected from the group consisting of halo, C₁-C₄ alkyl, C₁-C₄ alkoxy, cyano, nitro, C₃-C₄ cycloalkyl, C₂-C₄ alkenyl, trifluoromethyl, C₁-C₄ alkylthio, di(C₁-C₄ alkyl)amino, phenyl, benzyl, alkoxyalkyl of up to 4 carbons, —COOSi(CH₃)₃ and —(CH₂)ₙCOOSi(CH₃)₃ in which n is 1, 2 and 3, said sulfur atom in —S—Z being connected to a carbon atom of said heterocyclic ring Z include the following:

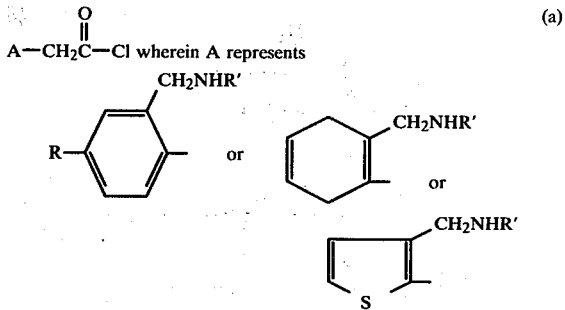

wherein R is hydrogen, hydroxy or methoxy and R' is hydrogen or methyl and the amino group is blocked, if desired, by conventional blocking groups including particularly by protonation;

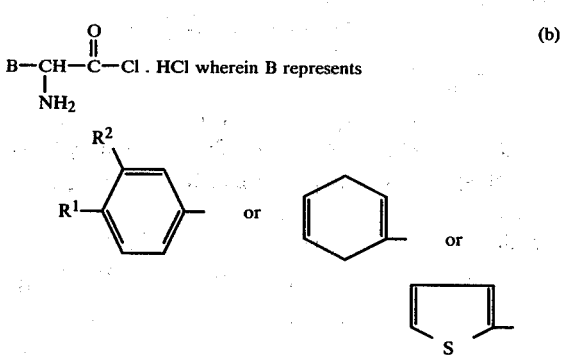

wherein R¹ is hydrogen, hydroxy or acetoxy and R² is hydrogen, chloro or hydroxy when R¹ is hydroxy and R² is hydrogen when R¹ is hydrogen or acetoxy;

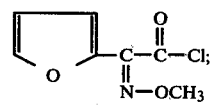

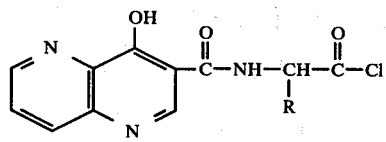

wherein R is phenyl, 4-hydroxyphenyl, 3,4-dihydroxyphenyl or cyclohexa-1,4-dien-1-yl;

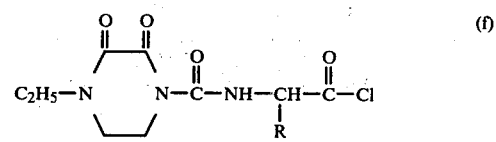

wherein R is phenyl, 4-hydroxyphenyl, 3,4-dihydroxyphenyl or cyclohexa-1,4-dien-1-yl;

(g) 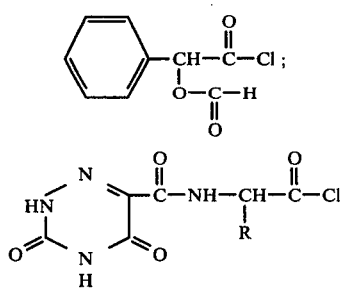

(h) 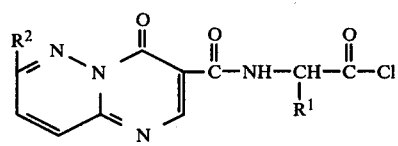

wherein R is phenyl, 4-hydroxyphenyl, 3,4-dihydroxyphenyl or cyclohexadien-1-yl (i) 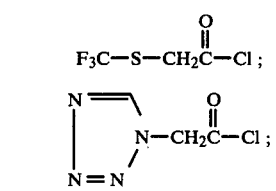

wherein $R^1$ is phenyl, 4-hydroxyphenyl, 3,4-dihydroxyphenyl or cyclohexadien-1-yl and $R^2$ is hydrogen or hydroxy;

(j) 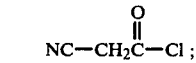

(k) 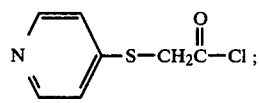

(l) 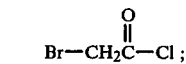

(m) 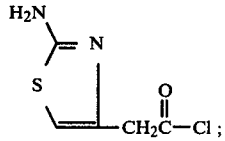

(n) 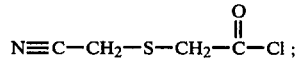

(o) 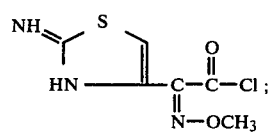

(p) 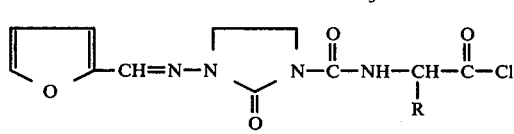

(q) 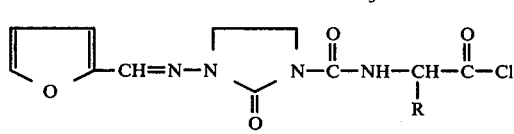

(r) 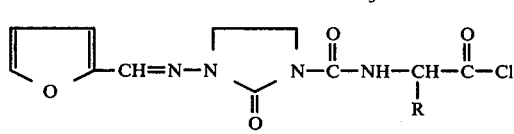

wherein R is phenyl, 4-hydroxyphenyl, 3,4-dihydroxyphenyl or cyclohexadien-1-yl;

(s) 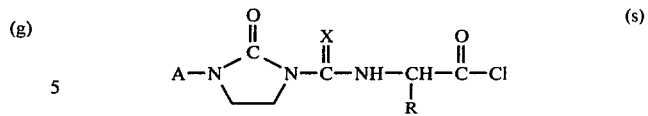

wherein A is hydrogen or alkyl of 1 to 4 carbon atoms or $CH_3SO_2-$, X is oxygen or sulfur and R is phenyl, 4-hydroxyphenyl, 3,4-dihydroxyphenyl or cyclohexa-1,4-dien-1-yl;

(t) 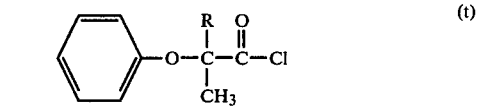

wherein R is hydrogen or methyl;

(u) 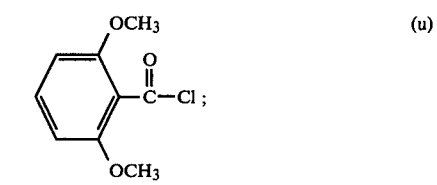

(v) 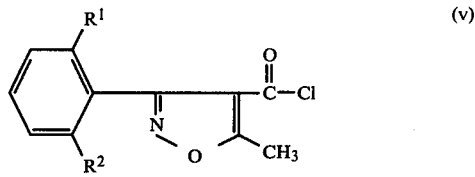

wherein each of $R^1$ and $R^2$ is hydrogen, chloro or fluoro;

(w) 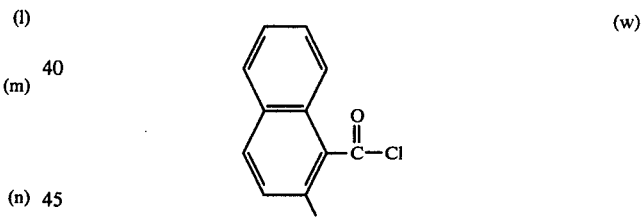

(x) 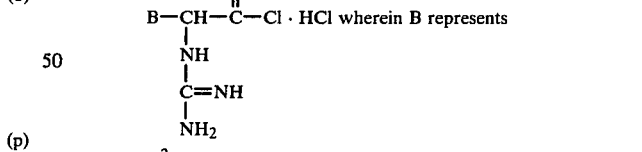

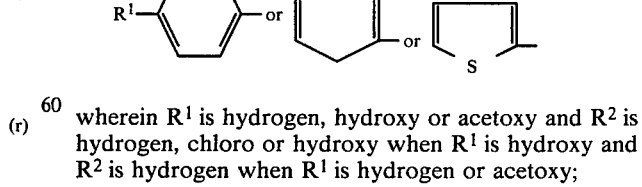

wherein $R^1$ is hydrogen, hydroxy or acetoxy and $R^2$ is hydrogen, chloro or hydroxy when $R^1$ is hydroxy and $R^2$ is hydrogen when $R^1$ is hydrogen or acetoxy;

(y) 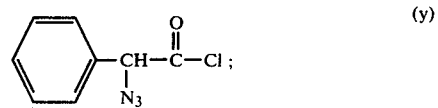

-continued (z) 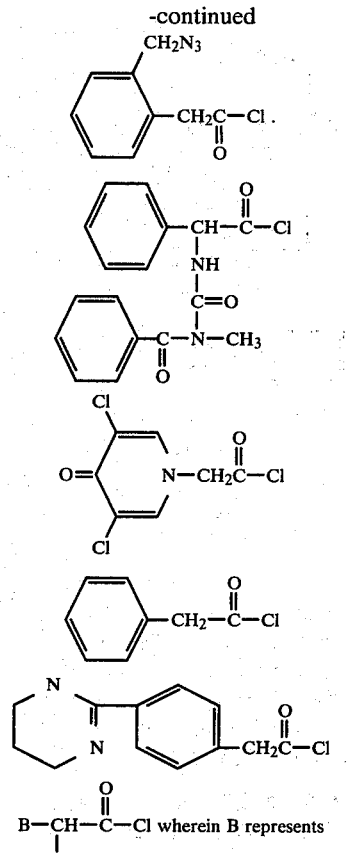

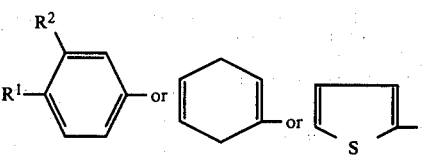

wherein R¹ is hydrogen, hydroxy or acetoxy and R² is hydrogen, chloro or hydroxy when R¹ is hydroxy and R² is hydrogen when R¹ is hydrogen or acetoxy, and R is hydrogen or cyanomethyl;

(ff) 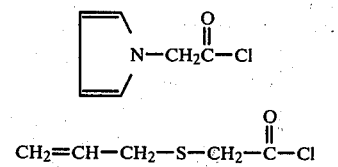

(gg) CH₂=CH—CH₂—S—CH₂—C(=O)—Cl (hh) 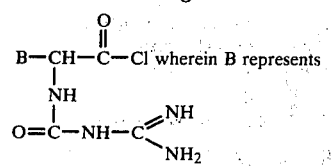

(ii) B—CH(NH—C(=O)—NH—C(=NH)NH₂)—C(=O)—Cl wherein B represents

-continued (aa) 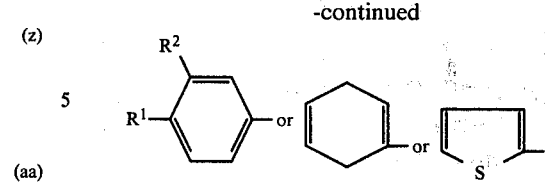

wherein R¹ is hydrogen, hydroxy or acetoxy and R² is hydrogen, chloro or hydroxy when R¹ is hydroxy and R² is hydrogen when R¹ is hydrogen or acetoxy;

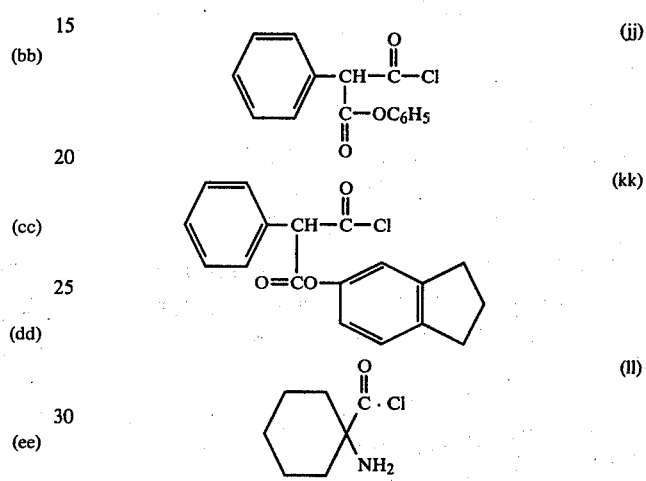

and the amino group is blocked, if desired, by conventional blocking groups including particularly by protonation;

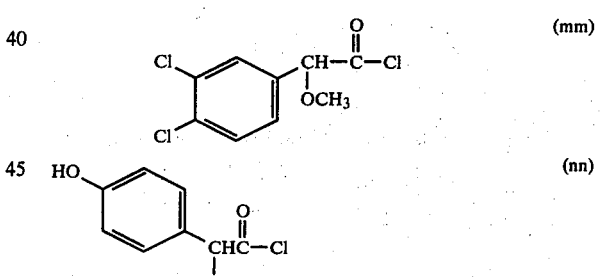

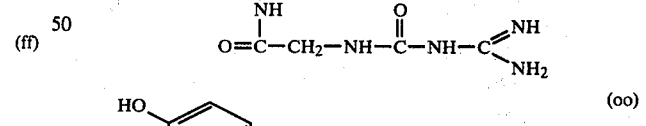

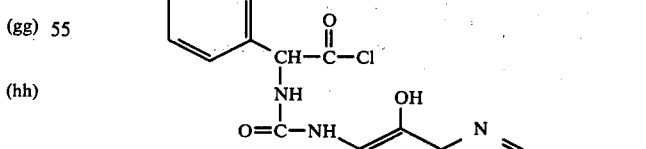

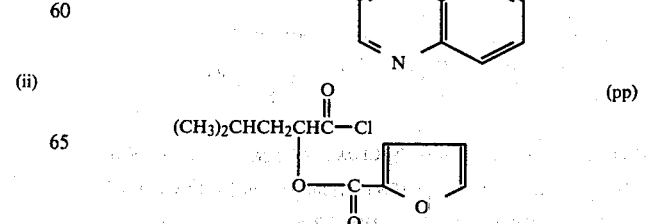

(qq) [structure: PhCH(N(CH3)NH2)C(O)Cl as the hydrochloride, if desired]

(rr) B—CH(NH—C(=O)—[thiopyranone])—C(O)—Cl wherein B represents

[structures: substituted phenyl with R¹, R²; cyclohexadienyl; thienyl]

wherein R¹ is hydrogen, hydroxy or acetoxy and R² is hydrogen, chloro or hydroxy when R¹ is hydroxy and R² is hydrogen when R¹ is hydrogen or acetoxy;

(ss) B—CH(NH—C(=O)—CH2NH—C(=NH)—[4-pyridyl])—C(O)—Cl wherein B represents

[structures: substituted phenyl with R¹, R²; cyclohexadienyl; thienyl]

wherein R¹ is hydrogen, hydroxy or acetoxy and R² is hydrogen, chloro or hydroxy when R¹ is hydroxy and R² is hydrogen when R¹ is hydrogen or acetoxy;

(tt) B—CH(NH—C(=O)—[4-hydroxypyridyl with CH=N-piperazinyl-N-CHO])—C(O)—Cl wherein B represents

[structures: substituted phenyl with R¹, R²; cyclohexadienyl; thienyl]

wherein R¹ is hydrogen, hydroxy or acetoxy and R² is hydrogen, chloro or hydroxy when R¹ is hydroxy and R² is hydrogen when R¹ is hydrogen or acetoxy;

(uu) [structure: 2,6-dichlorophenyl-pyrazole-4-methyl-3-carbonyl chloride]

(vv) [structure: thienyl-CH(C(=O)—O—4-tolyl)—C(O)—Cl]

Acid chlorides are normally prepared under vigorous conditions, as by treatment of the acid at reflux with thionyl chloride, but when sensitive groups are present, including sensitive blocking groups, they can be prepared under practically neutral conditions by reaction of a salt of the acid with oxalyl chloride.

DESCRIPTION OF THE PREFERRED EMBODIMENTS

CHEMISTRY

7-ADCA (7-aminodesacetoxycephalosporanic acid; also called 7-aminodecephalosporanic acid herein)
+ TEA (triethylamine)
+ TMCS (trimethylchlorosilane)

↓ in $CH_2Cl_2$ $(CH_3)_3SiNH$—[β-lactam-thiazine structure with $CH_3$ and $CO_2Si(CH_3)_3$]   + TEA · HCl (named below as Bis-trimethylsilyl 7-aminodecephalosporanic ester)

↓ $CO_2$ gas at 20° C.

$(CH_3)_3Si$—O—C(=O)—NH—[β-lactam-thiazine structure with $CH_3$ and $CO_2Si(CH_3)_3$]

(named below as trimethylsilyloxycarbonyl 7-aminodecephalosporanic acid TMS ester)

+ R—[phenyl]—CH($NH_3^+Cl^-$)—C(=O)—Cl + propylene oxide ↓

-continued

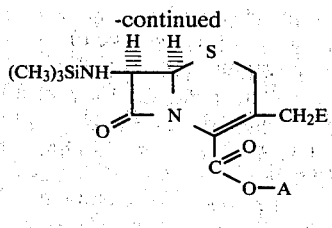

wherein
A is (CH₃)₃Si—, and
E has the same meaning as above, and then converting group A to hydrogen,
the improvement which comprises, prior to acylation, converting said silylated nucleus to a compound of the formula

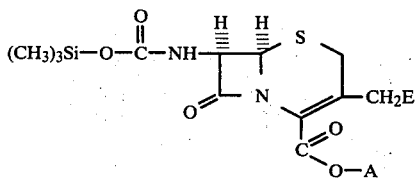

wherein A and E have the same meaning as above, by adding dry carbon dioxide to a solution of said silylated nucleus in an anhydrous inert organic solvent at a temperature in the range of 0° C. to 100° C. until completion of the carboxylation reaction.

EXAMPLE 1

Preparation of Bis-trimethylsilyl 7-Aminodecephalosporanic Acid Ester

A suspension of 7-ADCA (also called 7-aminodesacetoxycephalosporanic acid or 7-aminodecephalosporanic acid) (10 g., 46.68 mmole) in dry methylene chloride (100 ml.) was treated with trimethylchlorosilane (11.8 g., 13.7 ml., 108 mmole) (TMCS) followed by triethylamine (10.86 g., 14.4 ml., 107 mmole) (TEA) dropwise during 30 minutes. The reaction mixture was stirred for another two hours at 25° C. The reaction mix was then analyzed for complete silylation by NMR analysis. NMR indicated the integral ratio of —CO₂SiMe₃ and 7-NHSiMe₃ was 468:462. 100% conversion was thus obtained.

EXAMPLE 2

Preparation of Trimethylsilyloxycarbonyl 7-Aminodecephalosporanic Acid TMS Ester The reaction mixture of bis-trimethylsilyl-7-aminodecephalosporanic acid ester was then gassed with carbon dioxide at 25° C. for four hours with agitation and analyzed for complete carboxylation by NMR. 95% conversion was obtained.

EXAMPLE 3

Preparation of 7(D-α-Amino-p-hydroxyphenylacetamido)-3-methyl-3-cephem-4-carboxylic Acid (Cefadroxil) DMF Complex from Trimethylsilyloxycarbonyl 7-Aminodecephalosporanic Acid TMS Ester Trimethylsilyloxycarbonyl 7-aminodecephalosporanic acid TMS mixture (46.68 mmoles) containing triethylamine HCl was stirred and cooled to 5° C. The slurry was treated with propylene oxide (3.7 ml., 52.7 mmoles). D-(—)-2-(4'-Hydroxyphenyl)glycyl chloride HCl hemidioxane solvate (13.7 g., 48.7 mmoles) in five portions was added at 5° C. over three hours with good stirring. The mixture was further stirred at 5° C. for two hours. No solid acid chloride remained in the reaction mix. The final acylation mix was treated with methanol (5 ml.) followed by ice water (60 ml.). The pH was adjusted to pH 2.3 with triethylamine while maintaining the temperature at 5° C. The aqueous phase was separated, polish filtered on a filter precoated with diatomaceous earth ("Dicalite") and washed with water (15 ml.). The filtrate and wash was adjusted to pH 4.5 with triethylamine and isopropanol (100 ml.) and N,N-dimethylformamide (220 ml.) were added. The mixture was seeded with 10 mg. of cefadroxil DMF complex and allowed to crystallize at 25° C. for seven hours with agitation. The product was collected and washed with dimethylformamide (DMF; 20 ml.) and acetone (2×20 ml.) 11.51 g. of white crystalline cefadroxil DMF complex was obtained in 55.96% yield. NMR and IR were identical to a standard sample. NMR showed 1.9 moles DMF per mole of cefadroxil.

EXAMPLE 4

Preparation of 7-(D-α-Amino-α-phenylacetamido)-3-methyl-3-cephem-4-carboxylic Acid (Cephalexin)

Trimethylsilyloxycarbonyl 7-aminodecephalosporanic acid TMS ester (46.68 mmoles) containing triethylamine HCl was stirred and cooled to 5° C. The slurry was treated with propylene oxide (3.7 ml., 52.7 mmoles). D-(—)-Phenylglycyl chloride HCl (10.2 g., 47.5 mmoles) was added in five portions at 5° C. over 5 hours with good stirring. The mixture was further stirred for two hours at 5° C. Thin layer chromatography (TLC) showed incomplete acylation. The reaction mix was then warmed to 25° C. and stirred for one hour. The final acylation mix was treated with water (50 ml.). The pH was adjusted to 1.4 with stirring at 25° C. for 20 minutes. The aqueous phase was separated, polish filtered with diatomaceous earth ("Dicalite") and the filter cake washed with water (15 ml.). DMF (10 ml.) was added to the rich, polished aqueous portion. The aqueous solution was then heated to 60°–63°0 C. and treated with triethylamine (11 ml.) over 15 minutes to maintain pH at 4.0. The crystalline slurry so produced was then stirred at 5°–10° C. for one hour. The product was collected by filtration and washed with water (10 ml.) and 15 ml. isopropanol-water mixture (4:1). 4.40 gm. of cephalexin.H₂O was thus obtained. NMR and IR were comparable to the reference standard.

EXAMPLE 5

Cephaloglycin is produced by following the procedures of 1, 2 and 3 with substitution of an equimolar weight of 7-aminocephalosporanic acid (7-ACA) for the 7-aminodecephalosporanic acid (7-ADCA) used therein.

EXAMPLE 6

The cephalosporin having the formula

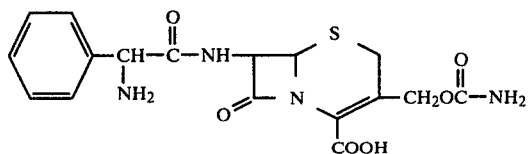

is produced by following the procedures of Examples 1, 2 and 3 with substitution for the 7-ADCA used therein of an equimolar weight of the compound having the formula

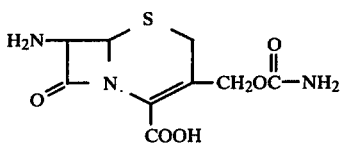

EXAMPLE 7

Cephalothin is produced by following the procedure of Example 5 except that the 2-phenylgycyl chloride hydrochloride used therein is replaced by an equimolar weight of 2-thienylacetyl chloride.

EXAMPLE 8

Reaction according to the above procedures of a compound having the formula

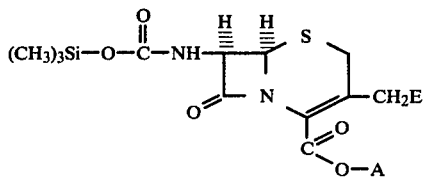

wherein

A is $(CH_3)_3Si-$ or an easily cleavable ester protecting group; and

E is hydrogen,

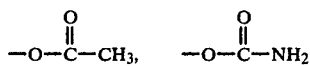

or $-S-Z$ wherein Z represents a 5- or 6-membered aromatic heterocyclic ring containing two, three or four atoms of N and zero or one atom selected from the group consisting of O and S, said heterocyclic ring being optionally substituted by one or two substituents selected from the group consisting of halo, $C_1-C_4$ alkyl, $C_1-C_4$ alkoxy, cyano, nitro, $C_3-C_4$ cycloalkyl, $C_2-C_4$ alkenyl, trifluoromethyl, $C_1-C_4$ alkylthio, di($C_1-C_4$ alkyl)amino, phenyl, benzyl, alkoxyalkyl of up to 4 carbons, $-COOSi(CH_3)_3$ and $-(CH_2)_nCOOSi(CH_3)_3$ in which n is 1, 2 or 3, said sulfur atom in $-S-Z$ being connected to a carbon atom of said heterocyclic ring Z, wherein E is the appropriate group for the desired final product with the appropriate acid chloride or acid chloride hydrochloride, said reagent containing blocking groups as necessary, followed by removal of any blocking groups including A whose removal is desired produces the following compounds:

BRL-16931 having the formula

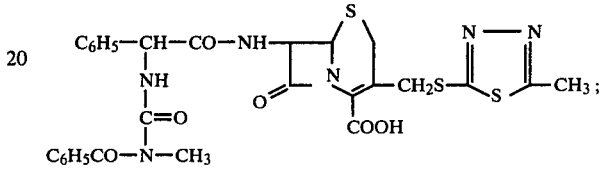

cephacetrile; cefaparole; cefatrizine; cefazaflur; cefazedone; ceforanide; ceftezole; cefuroxime; cephalothin; cephanone; cefaloram; cephapirin; cephradine; cefaclor; FR-10612 having the formula

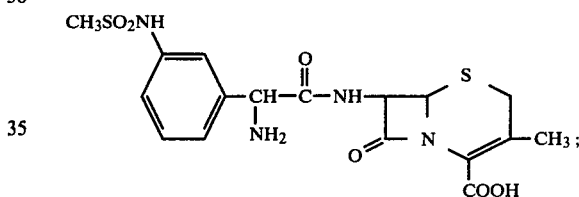

HR-580 having the formula

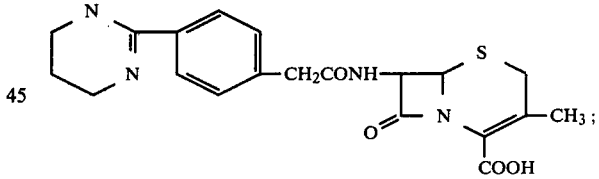

cefotaxime; PC-518 having the formula

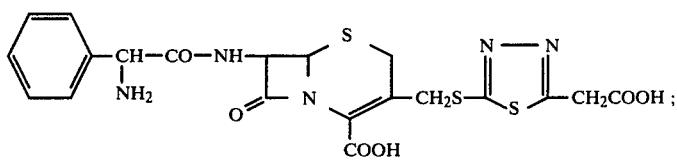

SCE-1365 having the formula

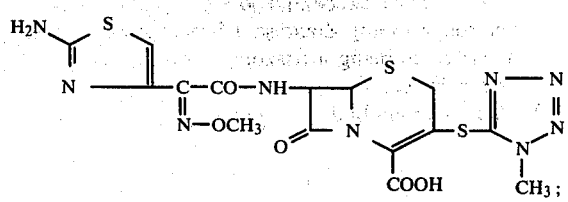

sigmacef (ST-21); SQ-14448 having the formula

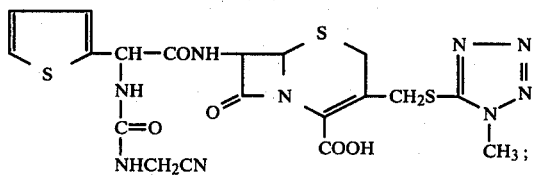

SQ-67590 having the formula

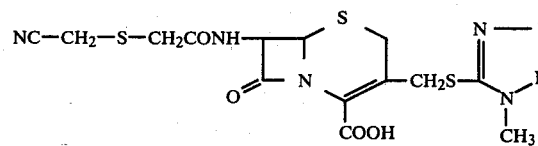

SQ-69613 having the L (S) configuration and the formula

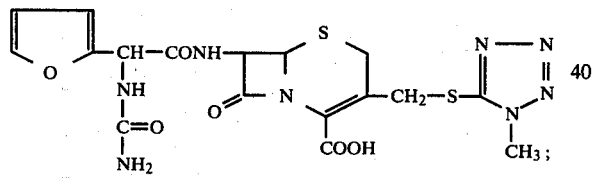

T-1551 having the formula

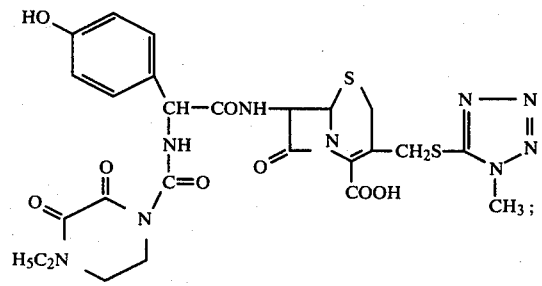

the compound having the formula

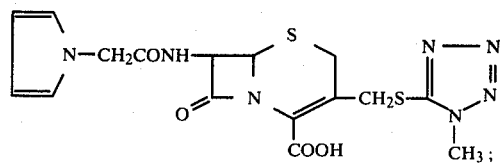

-continued

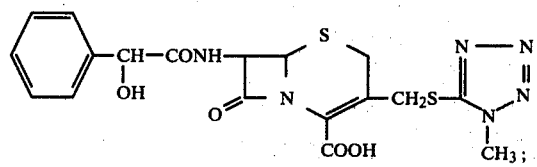

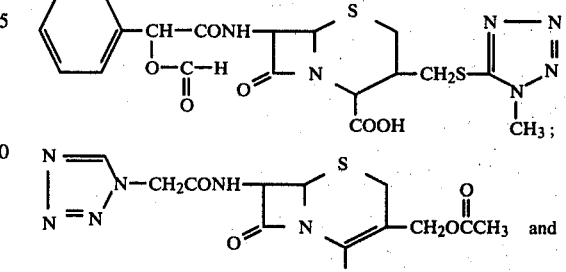

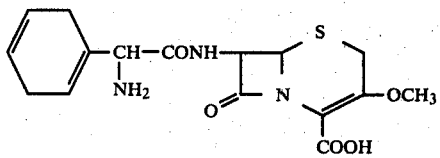

This invention is capable of industrial application.

We claim:

1. A compound having the formula

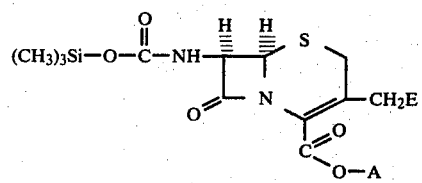

wherein

A is an easily cleavable ester protecting group; and
E is —S—Z wherein Z represents a 5-membered aromatic heterocyclic ring containing three or four atoms of N and zero or one atom selected from the group consisting of O and S, said heterocyclic ring being substituted by one substituent selected from the group consisting of methyl and —(CH$_2$)$_n$COOSi(CH$_3$)$_3$ in which n is 1, 2 or 3, said sulfur atom in —S—Z being connected to a carbon atom of said heterocyclic ring Z and said 5-membered aromatic heterocycle being a triazole, tetrazole, oxadiazole or thiadiazole.

2. A compound having the formula

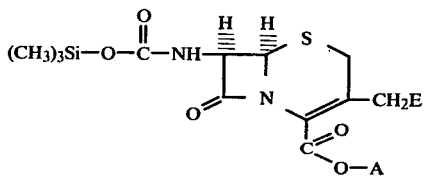

wherein
A is (CH₃)₃Si— and
E is —S—Z wherein Z represents a 5-membered aromatic heterocyclic ring containing three or four atoms of N and zero or one atom selected from the group consisting of O and S, said heterocyclic ring being substituted by one substituent selected from the group consisting of methyl and —(CH₂)-

$_n$COOSi(CH₃)₃ in which n is 1, said sulfur atom in —S—Z being connected to a carbon atom of said heterocyclic ring Z and said 5-membered aromatic heterocycle being a triazole, tetrazole, oxadiazole or thiadiazole.

3. The compound having the formula

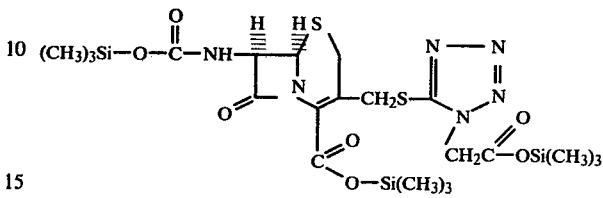

* * * * *